US00PP23252P2

(12) United States Plant Patent
Bergman

(10) Patent No.: US PP23,252 P2
(45) Date of Patent: Dec. 11, 2012

(54) ***CHRYSANTHEMUM* PLANT NAMED 'CIDZ0007'**

(50) Latin Name: *Chrysanthemum×morifolium*
Varietal Denomination: CIDZ0007

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/136,556

(22) Filed: Aug. 4, 2011

(51) Int. Cl.
*A01H 5/00* (2006.01)

(52) U.S. Cl. ..... Plt./293

(58) Field of Classification Search ..... Plt./293
See application file for complete search history.

*Primary Examiner* — Annette Para
(74) *Attorney, Agent, or Firm* — Joshua L. Price

(57) ABSTRACT

A new *Chrysanthemum* plant named 'CIDZ0007' particularly distinguished by the dark red ray floret color, large and loose semi-incurved decorative inflorescence form, medium-dark foliage color, and an eight week flowering response.

1 Drawing Sheet

Latin name of the genus and species of the plant claimed: *Chrysanthemum×morifolium.*

Varietal denomination: 'CIDZ0007'.

BACKGROUND OF THE NEW PLANT

The present invention comprises a new *Chrysanthemum*, botanically known as *Chrysanthemum×morifolium*, and hereinafter referred to by the variety name 'CIDZ0007'.

'CIDZ0007' is a product of a planned breeding program. The new cultivar has dark red ray floret color, large and loose semi-incurved decorative inflorescence form, medium-dark foliage color, and an eight week flowering response.

'CIDZ0007' originated from a hybridization made in June 2006 in a controlled breeding environment in Salinas, Calif., USA. The female parent was the proprietary plant designated 'YB-6483', unpatented, with red decorative flowers, few disc florets and a taller plant habit.

The male parent of 'CIDZ0007' was an unpatented proprietary plant identified as 'YB-A8021' with red decorative flowers, an open centered inflorescence with pollen and a more compact growth habit. The resultant seed was sown in October 2006 in Fort Myers, Fla., USA.

'CIDZ0007' was selected as one flowering plant within the progeny of the stated cross in March 2007 in a controlled environment in Fort Myers, Fla., USA.

The first act of asexual reproduction of 'CIDZ0007' was accomplished when vegetative cuttings were propagated from the initial selection in June 2007 in a controlled environment in Fort Myers, Fla., USA.

BRIEF SUMMARY OF INVENTION

Horticultural examination of plants grown from cuttings of the plant initiated in June 2007, and continuing thereafter, has demonstrated that the combination of characteristics as herein disclosed for 'CIDZ0007' are firmly fixed and are retained through successive generations of asexual reproduction.

'CIDZ0007' has not been observed under all possible environmental conditions. The phenotype may vary significantly with variations in environment such as temperature, light intensity and day length.

A Plant Breeder's Right for this cultivar was applied for in Canada on Aug. 17, 2010 (10-7065). 'CIDZ0007' has not been made publicly available more than -one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIDZ0007' with colors being as true as possible with an illustration of this type. The photographic drawing shows four flowering potted plants of the new variety and a close-up of the flowers.

DETAILED BOTANICAL DESCRIPTION

The plant descriptions, measurements and aforementioned photographs were taken in Gilroy, Calif. in mid-May 2011 under natural light. These plants were propagated and grown in Nipomo, Calif. and shipped to Gilroy, Calif. for the data collection and photographs. These plants were approximately 11 weeks of age; grown as four plants together in a six inch pot under greenhouse trial conditions.

Color references are made to The Royal Horticultural Society Colour Chart (R.H.S.) 2001.

TABLE 1

DIFFERENCES BETWEEN THE NEW VARIETY 'CIDZ0007' AND A SIMILAR VARIETY

| | 'CIDZ0007' | 'Yoharvard' (U.S. Plant Pat. No. 19,688) |
|---|---|---|
| Inflorescence diameter: | Larger | Smaller |
| Ray floret length: | Longer | Shorter |

TABLE 1-continued

DIFFERENCES BETWEEN THE NEW VARIETY 'CIDZ0007' AND A SIMILAR VARIETY

| | 'CIDZ0007' | 'Yoharvard' (U.S. Plant Pat. No. 19,688) |
|---|---|---|
| Ray floret color: | More red | More greyed-purple |
| Foliage length: | Shorter | Longer |
| Phyllaries quantity: | More | Less |

Plant:

*Form, growth and habit*.—Herbaceous pot-type, stems upright, strong and moderately vigorous growth habit.

*Plant height*.—About 21.-24.0 cm.

*Plant height* (*inflorescence included*).—About 27.-31.0 cm.

*Plant width*.—About 17.-21.0 cm.

Roots:

*Number of days to initiate roots*.—About 4 days at about 22 degrees C.

*Number of days to produce a rooted cutting*.—About 10-12 days at 22 degrees C.

*Type*.—Fine, fibrous, free branching.

*Color*.—RHS N155B but whiter.

Foliage:

*Arrangement*.—Alternate, simple.

*Immature, leaf color, upper surface*.—RHS 139A but lighter.

*Lower surface*.—RHS 139C.

*Mature, leaf color, upper surface*.—RHS 139A but lighter.

*Lower surface*.—RHS 139C.

*Length*.—7.2-9.5 cm.

*Width*.—5.2-6.2 cm.

*Shape*.—Ovate.

*Base shape*.—Attenuate.

*Apex shape*.—Mucronulate.

*Margin*.—Palmately lobed; irregularly serrate.

*Texture, upper surface*.—Bifid T-shaped hairs.

*Lower surface*.—Bifid T-shaped hairs.

*Color of veins, upper surface*.—RHS 146B.

*Color of veins, lower surface*.—RHS 146B.

*Petiole color*.—RHS 146B.

*Length*.—1.8-2.3 cm.

*Diameter*.—0.2-0.3 cm.

*Texture*.—Bifid T-shaped hairs.

Stem:

*Quantity of main branches per plant*.—3-6.

*Color of stem*.—RHS 138A but appears lighter, with the upper portions having some anthocyanins of shades of RHS N187A and lighter.

*Length of stem*.—24-32 cm.

*Diameter*.—0.5-0.6 cm.

*Length of internodes*.—2.0-5.0 cm.

*Texture*.—Bifid T-shaped hairs.

*Color of peduncle*.—Shades of RHS N187A and lighter, but appears lighter due to hairs.

*Length of peduncle*.—1.7-2.1 cm.

*Peduncle diameter*.—0.5 cm.

*Texture*.—Bifid T-shaped hairs.

Inflorescence:

*Type*.—Compositae type, solitary decorative semi-in-curved inflorescences borne terminally above foliage, ray florets arranged acropetally on a capitulum.

*Quantity of short days to flowering* (*response time*).—About 8 weeks.

*Quantity of inflorescences per plant*.—3-6.

*Lastingness of individual blooms on the plant*.—About 4 weeks.

*Fragrance*.—Slightly spicy.

Bud (just when opening/showing color):

*Color*.—None observed at time of data collecting.

*Length*.—N/A.

*Width*.—N/A.

*Shape*.—N/A.

Immature inflorescence:

*Diameter*.—8.-10.5 cm.

*Color of ray florets, upper surface*.—RHS 46A with deeper, darker streaks longitudinally.

*Lower surface*.—RHS 187C with darker streaks.

Mature inflorescence:

*Diameter*.—14.-15.0 cm.

*Depth*.—4.0 cm.

*Total diameter of 'disc'*.—Visually indistinct.

*Receptacle height*.—0.8-0.9 cm.

*Receptacle diameter*.—1.2 cm.

Ray florets:

*Average quantity of florets*.—Approximately 300 in numerous whorls.

*Color of florets, upper surface*.—RHS 46A but deeper, darker and much more velvety looking.

*Lower surface*.—RHS 185B.

*Length*.—5.4-7.8 cm.

*Width*.—1.1-1.3 cm.

*Shape*.—Elliptical.

*Apex shape*.—Obtuse to slightly praemorse.

*Margin*.—Entire.

*Texture, upper surface*.—Papillose.

*Lower surface*.—Papillose.

Disc florets:

*Average quantity of florets*.—3-7.

*Color of florets*.—RHS 1C basally, RHS 12A apex.

*Length*.—0.4-0.5 cm.

*Width*.—0.1 cm.

*Shape*.—Tubular, elongated.

*Apex shape*.—Acute, 5 pointed.

Phyllaries:

*Quantity*.—Approximately 30.

*Color, upper surface*.—RHS 137D.

*Lower surface*.—RHS 137C but appears lighter due to hairs.

*Length*.—1.0-1.4 cm.

*Width*.—0.2-0.25 cm.

*Shape*.—Lanceolate.

*Apex shape*.—Acute.

*Base*.—Fused.

*Margins*.—Entire, some with RHS 166A margins.

*Texture, upper surface*.—Glabrous.

*Lower surface*.—Bifid T-shaped hairs.

Reproductive organs:

*Pistil*.—1.

*Found on both florets*.—Yes.

*Length*.—0.8 cm.

*Style color*.—RHS 1C.

*Style length*.—0.7 cm.

*Stigma color*.—RHS 6A.

*Stigma shape*.—Bi-parted.

*Ovary color*.—Not observed.

*Stamens*.—4.

*Found on only disc florets*.—Yes.
*Color of filaments*.—RHS C155C.
*Length filaments*.—0.3-0.4 cm.
*Anther color*.—RHS 6B.
*Anther length*.—0.1 cm.
*Anther shape*.—Oblong.
*Color of pollen*.—RHS 9B.
*Pollen amount*.—Abundant per anther.
*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'CIDZ0007' substantially as illustrated and described herein.

* * * * *

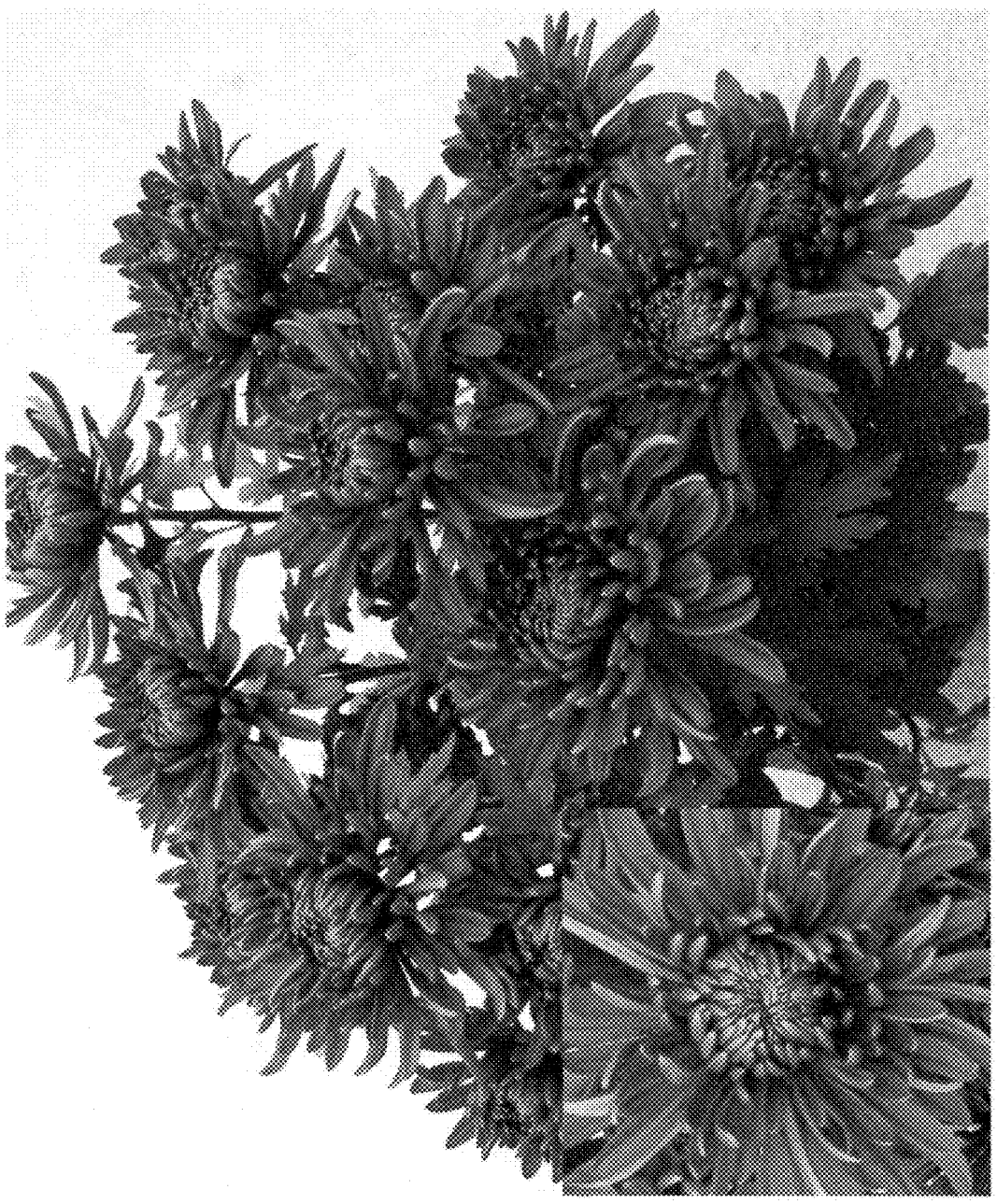

UNITED STATES PATENT AND TRADEMARK OFFICE

CERTIFICATE OF CORRECTION

PATENT NO. : PP23,252 P2
APPLICATION NO. : 13/136556
DATED : December 11, 2012
INVENTOR(S) : Bergman It is certified that error appears in the above-identified patent and that said Letters Patent is hereby corrected as shown below:

At column 2, line 7, delete "-one" and insert therefor --one--

At column 5, line 2, delete "C155C" and insert therefor --155C--

Signed and Sealed this
Fifth Day of February, 2013

Teresa Stanek Rea
*Acting Director of the United States Patent and Trademark Office*